United States Patent [19]
Yelland et al.

[11] Patent Number: 5,054,479
[45] Date of Patent: Oct. 8, 1991

[54] SAFETY VISOR HAVING A ROTATABLY MOUNTED SHIELD AND FILTER

[75] Inventors: David R. Yelland, Redhill; John G. Gilbert, Reigate; John Ewans, High Wycombe, all of United Kingdom

[73] Assignee: Pulsafe Safety Products Limited, United Kingdom

[21] Appl. No.: 336,338

[22] Filed: Apr. 11, 1989

[30] Foreign Application Priority Data

Apr. 19, 1988 [GB] United Kingdom ............... 8809221

[51] Int. Cl.$^5$ .......................... A62B 7/10; A62B 9/04; A42B 3/00
[52] U.S. Cl. .......................... 128/201.25; 128/201.24; 128/202.27; 128/205.25; 128/206.12; 2/9; 2/436
[58] Field of Search .................. 128/201.13, 201.22, 128/201.23, 201.24, 201.25, 202.27, 204.18, 205.18, 205.25, 206.21, 206.24, 206.12; 2/435, 436, 9

[56] References Cited

U.S. PATENT DOCUMENTS

| | | | |
|---|---|---|---|
| 968,232 | 8/1910 | Bentz | 128/201.25 |
| 2,525,236 | 10/1950 | Palmer | 128/205.25 |
| 2,688,962 | 9/1954 | Summers | 128/201.15 |
| 3,822,698 | 7/1974 | Guy | 128/201.25 |
| 4,266,301 | 5/1981 | Canda | 2/171.3 |
| 4,280,491 | 7/1981 | Berg et al. | 128/201.25 |
| 4,549,542 | 10/1985 | Chien | 128/201.24 |
| 4,752,974 | 6/1988 | Haino | 128/201.24 |

FOREIGN PATENT DOCUMENTS

| | | | |
|---|---|---|---|
| 1212821 | 11/1970 | United Kingdom | 128/201.25 |
| 1426432 | 2/1976 | United Kingdom | 128/201.25 |
| 1495020 | 12/1977 | United Kingdom | 128/201.25 |
| 1564922 | 4/1980 | United Kingdom | 128/201.25 |
| 2032284 | 5/1980 | United Kingdom | 128/201.25 |
| 2061696 | 5/1981 | United Kingdom | 128/201.25 |
| 2063074 | 6/1981 | United Kingdom | 128/201.25 |
| 2153003 | 8/1985 | United Kingdom | 128/201.25 |
| 81/02514 | 9/1981 | World Int. Prop. O. | 128/201.25 |

*Primary Examiner*—Edgar S. Burr
*Assistant Examiner*—Kimberly L. Asher
*Attorney, Agent, or Firm*—Kinney & Lange

[57] ABSTRACT

A safety visor having a face screen (6) supported by a head-harness (1, 2), the face screen (6) having sealing means (22) to enclose the space between the face of a wearer and the face screen (6) and also having means (12) for providing a flow of clean air under elevated pressure to the space from above the face, in which the face screen (6) is provided with an upward extension (3) having a cavity which is connected to the space and is provided with a readily detachable unit (12) which can be attached to the cavity in an air tight manner, the unit (12) having an air filter (20) to be located within the cavity and a pump (36, 37) to pump ambient air through the filter (20) into the cavity and then into the space. The face screen (6) with the extension (3) is rotatable about the head-harness (1, 2) in order to allow the face screen (6) to be moved to an inoperable position above the head of a wearer when not required.

3 Claims, 3 Drawing Sheets

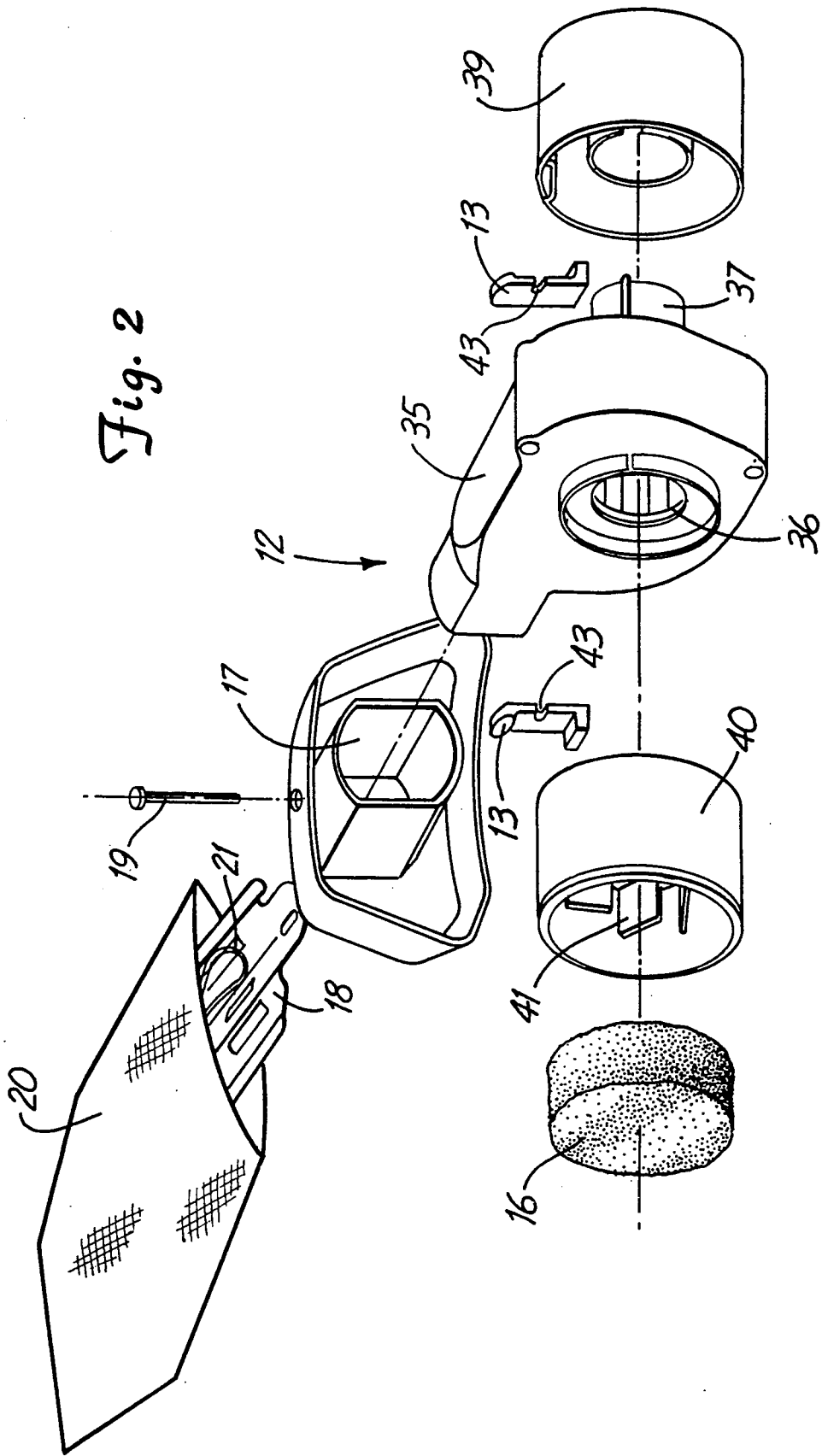

SAFETY VISOR HAVING A ROTATABLY MOUNTED SHIELD AND FILTER

This invention relates to safety visors.

It is known to use safety visors embodying means of respiratory protection when working in dusty atmospheres. Such visors embody sealing means to enclose the space between the face of the wearer and the visor and means to introduce clean air into the space. The sealing means may or may not be impermeable to air. The clean air source may be an air cylinder or air supplied by a delivery tube from a compressor or blower.

It is also known to provide helmets with a visor extension with sealing means between the face of the wearer and the visor and powered means within the helmet to force or draw air through a filter to deliver it at elevated pressure to the space between the face of the wearer and the visor.

In any such visor so far described it is usual that the air space between the wearer's face and the visor is at a pressure above that of the ambient environment to reduce the tendency for contaminated air to enter said space. Air in excess of that required for breathing may exit from said space by means of valves or holes fitted to the visor and/or face seal, or it may exit through any natural gaps between the periphery of the seal and the face, or it may exit through the seal itself if such seal is constructed of an air permeable material.

It is also known to provide a safety visor comprising a face screen which is rotatable about a head-harness between an operable and an inoperable position, and to supply pressurised air to the space between the face screen and the wearer's face when the face screen is in the operable position.

Various safety visors and helmets with visors as discussed above are disclosed in GB-A-1212821; GB-A-1564922; GB-A-1426432; GB-A-1495020; GB-A-2032284; GB-A-2061696; GB-A-2063074; U.S. Pat. No. 3822698; and WO81/02514.

According to this invention there is provided a safety visor comprising a head-harness to fit a wearer's head, a face screen carried by the harness and having sealing means to enclose the space between the face of a wearer and the face screen, and a supply means to provide a flow of clean air under elevated pressure to said space, in which the air supply means is mounted on an upward extension of the face screen, the face screen and the air supply means being rotatable as a unit about the harness between a operable position where the sealing means is in engagement with the face of a wearer and an inoperable position above the face of the wearer when not required Preferably the upward extension of the face screen has a cavity, the air supply means comprising a detachable unit which can be attached to the cavity in a gas-tight manner said unit having an air filter to be located in the cavity and a pump to pump ambient air through the filter into the cavity and hence into said space.

Preferably the detachable unit is removably located in the cavity by two spring clips which are inserted into corresponding slots in a wall of the cavity. The filter may be a bag filter.

The sealing means may be a foam material member which encloses said space by conforming the edges of the foam material member to the contours of the face of the wearer. A removable flexible hood may be provided to cover a wearer's head and neck.

A specific embodiment of a safety visor according to the invention will now be described by way of example with reference to the accompanying drawings, in which:

FIG. 2 is an exploded perspective view from the same angle as FIG. 1 of the combined pump and filter unit.

Figure 1:
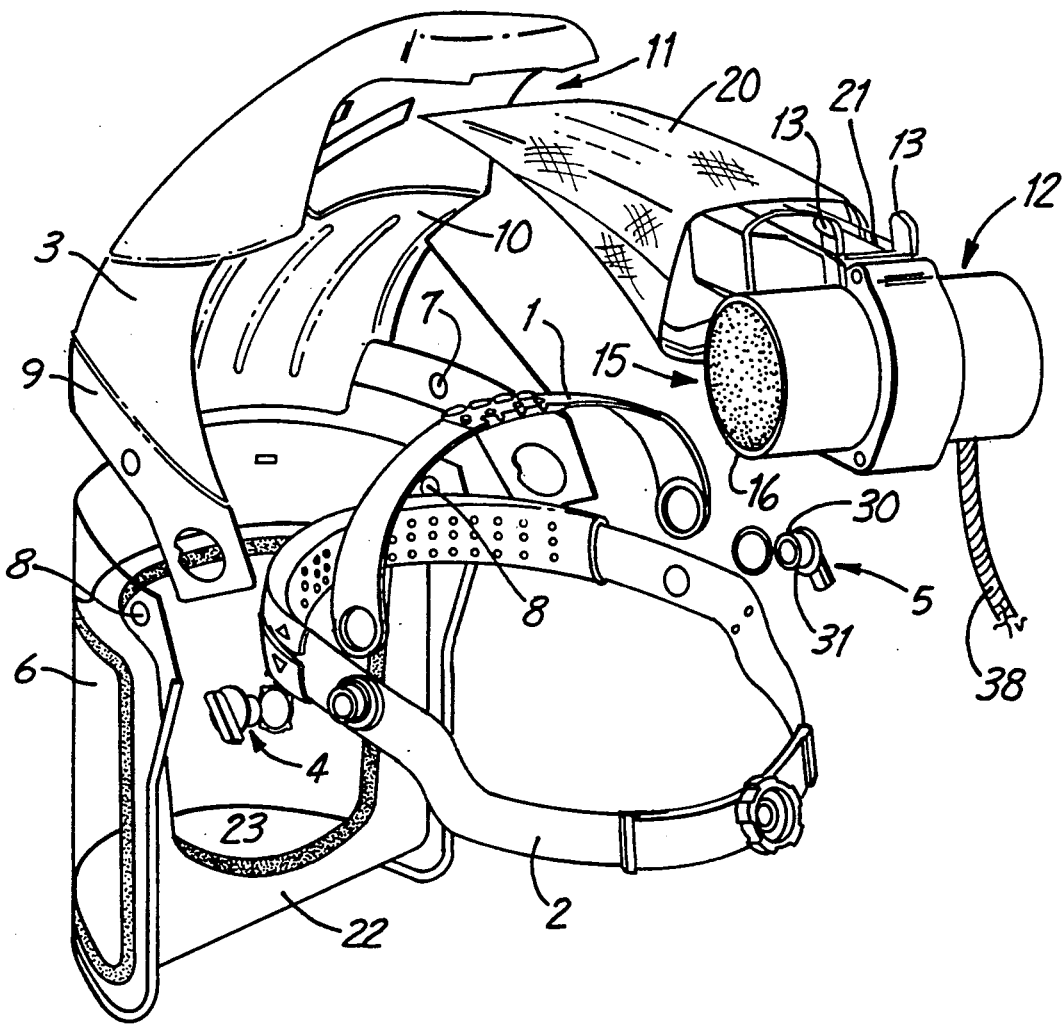
FIG. 1 is an exploded perspective view of the visor from one side and the rear.

Referring first of all to FIG. 1 the visor comprises an adjustable head-harness having a first adjustable band 1 to pass over the head and a second adjustable band 2 to pass around the head.

The visor comprises three main components which are attached to the head-harness, namely a face screen 6, a housing 3 which forms an upward extension of the face screen 6, and a combined pump and filter unit 12.

Figure 1A:
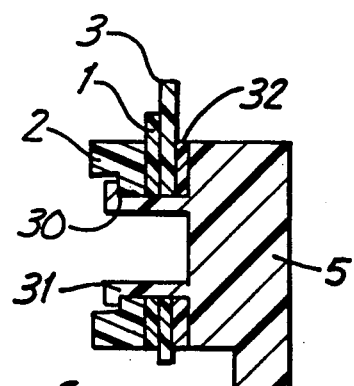
FIG. 1A is a scrap section through the attachment between the housing and head-harness.
Figure 3:
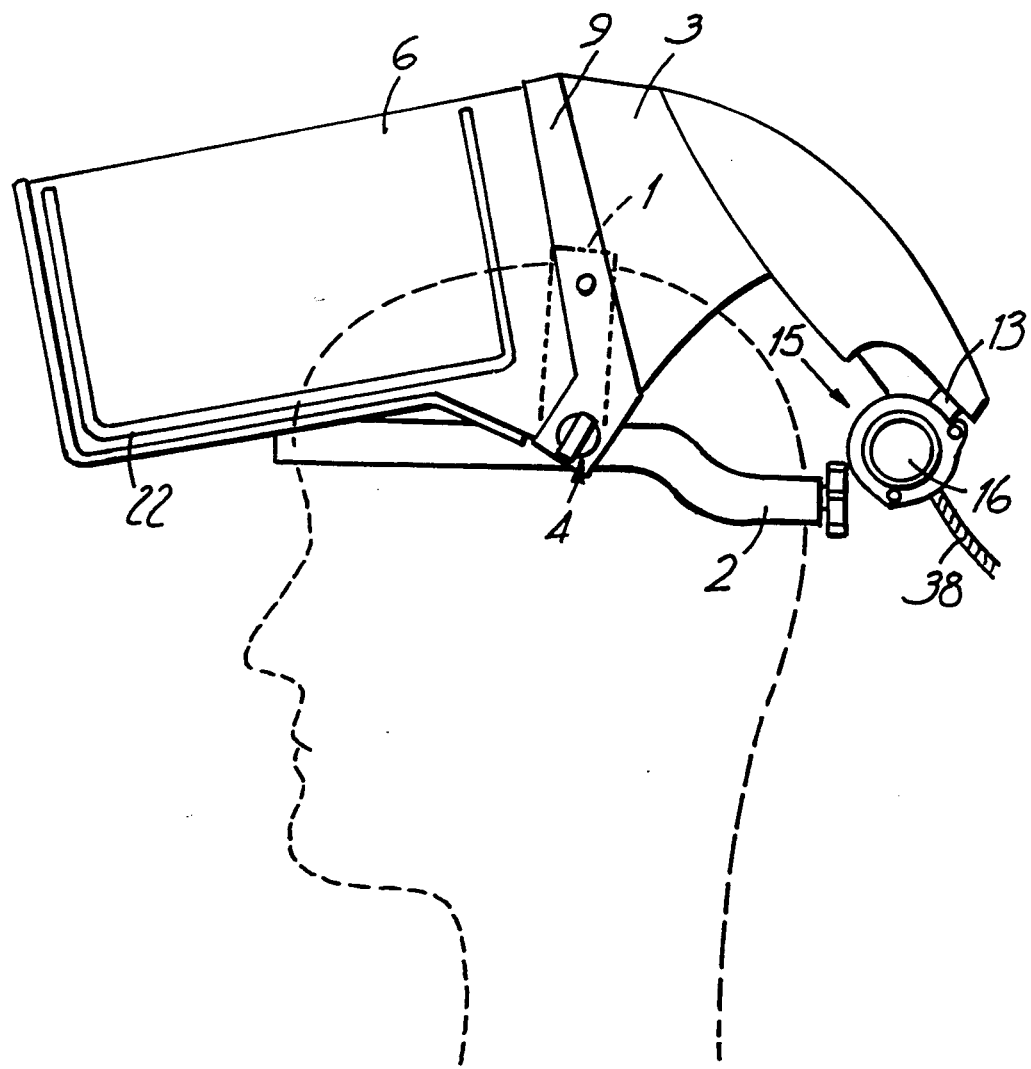
FIG. 3 is a side view of the visor of FIG. 1 with a face shield in a raised position.

The housing 3 is pivotally attached to the head-harness by means of screws 4 and 5 the subject of GB-A-2153003 which can be tightened or loosened and which allow the housing 3 to be rotated relative to the head-harness and hold the face screen 6 in an adjusted position. FIG. 1A is a scrap section through the screw 5 and the pieces that it attaches together. It may be seen that the screw 5 passes first of all through a locking washer 32, then through the housing 3, then through the head band 1 and then through the head band 2. Two lugs 30 and 31 engage with the inside of an annular surface on the head band 2, and the surface is cammed so that on rotation of the screw 5 the pieces are drawn together to secure them in position.

The housing 3 is made up of two principle pieces, an outer skin 9 which extends rearwardly to engage with the head-harness, and an inner skin 10, these two skins 9 and 10 being separated to form a cavity therebetween. The pump and filter unit 12 fits into the cavity as will be later described, and the face screen 6 is attached to the lower edge of the outer skin 9.

The face screen 6 is generally part cylindrical in shape and at its upper edge is provided with keyhole shaped slots 8 which engage with headed bosses 7 attached to the inner side of the outer skin 9. Thus, the face screen 6 is readily replaceable if damaged.

The face screen 6 is also provided with a shaped foam material sealing member 22 which is adhered to the face screen 6 and is shaped to engage around the face of a wearer of the visor to conform to the contours of the face of the wearer and define therewith a reasonably air-tight space.

The pump and filter unit 12 will now be described particularly having regard to FIG. 2. The pump has a main housing 35 which contains a centrifugal impeller 36 which is rotated by an electric motor 37. Power is supplied to the electric motor 37 from batteries or the like via a cord 38 (FIG. 1). The motor 37 is covered by an end cap 39.

Air is drawn into the impeller 36 through a cylindrical port member 40 containing a coarse fibre filter 16. The port member 40 contains blades 41 on which the filter 16 rests and which direct the air towards the impeller 36.

Attached to the upper side of the housing 35 are two spring clips 13 which are engagable in slots (not visible) at the upper edge of the outer skin 9 of the housing 3.

Air passing out of the housing 35 passes through a channel member 17 which is attached to the housing 35 and is provided with a removable pin 19 which locates a corrugated tongue 18 which supports a bag filter 20. The corrugations of the tongue 18 serve to hold the bag filter 20 open.

The bag filter 20 is provided with a resilient band 21 which engages around the clips 13 and is held in notches 43 in the clips 13. This enables the bag filter 20 to be readily removed.

It will be seen from FIG. 1 that the combined pump and filter unit 12 is shaped to slide into the cavity formed between the two skins 9 and 10 of the housing member 3 with the clips 13 engaged in the slots in the outer skin 9.

In use the visor is located on the head of the wearer by means of the head-harness and the foam material sealing member 22 fits closely against the sides of the wearer's face. The pump unit is turned on drawing air through the filter 16 which air is then filtered through the bag filter 20 and passes through the space between the cavity formed between the skins 9 and 10 of the housing 3 into the space between the wearer's face and the face screen 6. Because the air pressure provided by the pump is above atmospheric pressure the seal between the face screen and the wearer's face does not have to be a particularly good seal to ensure that the wearer breathes filtered air. If the wearer does not wish to have the face screen over his face at any particular time the whole unit comprising the face screen 6 and the pump and filter unit 12 in the cavity in the housing 3 may be rotated about the screws 5 to a position above the wearer's head which is an inoperative position.

The visor may be provided with a textile hood to protect the wearer's hair and neck from dust, with such textile hood being attached to two pop-fasteners at the top of the inner skin 10 of the housing 3 and to two velcro tapes along the upper edge of that part of the outer skin 9 which extends towards the screws 4 and 5. Thus, the textile hood is readily removable if not required, or for replacement.

We claim:

1. A safety visor comprising a head-harness to fit a wearer's head, a face screen carried by the harness and having sealing means to enclose the space between the face of the wearer and the face screen, and a supply means to provide a flow of clean air under elevated pressure to said space, in which the air supply means is mounted on an upward extension of the face screen and the air supply means is mounted at he end of the upward extension remote from the face screen, the face screen and the air supply means being rotatable as a unit about the harness between an operable position where the face screen covers the face of a wearer with the sealing means in engagement with the face of the wearer, and an inoperable position where the face screen is above the face of the wearer and the air supply means is behind the head of the wearer, the upward extension of the face screen having a cavity at said remote end, the air supply means comprising a detachable unit which can be attached to the cavity in a gas tight manner, said unit having an air filter to be located in the cavity and a pump to pump ambient air through the filter into the cavity and hence into said space, the air supply means detachable unit being removably located in the cavity by two spring clips which are inserted into corresponding slots in a wall defining the cavity.

2. A safety visor as claimed in claim 1 in which the filter is a bag filter.

3. A safety visor as claimed in claim 1, in which the sealing means is a foam material member which encloses said space by conforming the edges of the foam material member to the contours of the face of the wearer.

* * * * *